United States Patent [19]

Agrawal et al.

[11] Patent Number: 5,684,147
[45] Date of Patent: Nov. 4, 1997

[54] THERAPEUTIC ANTI-HIV ANTI-VIRAL OLIGONUCLEOTIDES AND PHARMACEUTICAL FORMULATIONS THEREOF

[75] Inventors: Sudhir Agrawal, Shrewsbury; Jin-Yang Tang, Worcester, both of Mass.

[73] Assignee: Hybridon, Inc., Cambridge, Mass.

[21] Appl. No.: 319,823

[22] Filed: Oct. 7, 1994

Related U.S. Application Data

[63] Continuation of Ser. No. 958,135, Oct. 5, 1992, abandoned.
[51] Int. Cl.$^6$ .................................................. C07H 21/04
[52] U.S. Cl. ........................... 536/24.5; 514/44; 435/238; 935/8; 935/33
[58] Field of Search ........................... 514/44; 536/23.1, 536/23, 72, 24.5; 435/238, 240.2; 935/8, 33

[56] References Cited

FOREIGN PATENT DOCUMENTS

0331939A2  2/1989  European Pat. Off.
WO 8908146  8/1989  European Pat. Off.

OTHER PUBLICATIONS

R Weiss (1991) Science News 139: 108–109.
CA Stein et al (1993) Science 261: 1004–1012.
N Miller et al (1994) Parasitology Today 10:92–97.
RA Stull et al (1995) Pharmaceutical Research 12:465–483.
S Wu–Pong (1994) Pharmaceutical Technology 118: 102–114.
RW Wagner (1994) Nature 372: 333–335.
JS Cohen (1992) Trends in Biotechnology 10: 87–91.
B Dropulic et al (1994) Human Gene Therapy 5: 927–939.
PA Pizzo et al (1994) Clinical Infectious Diseases 19: 177–196.

ER Kern (1990) In: Antiviral Agents and Viral Diseases of Man, 3rd edition, GJ Galasso et al, GJ Galasso et al, eds, pp. 94–95.
Sacramento Bee (Feb. 26, 1994) p. A22.
Sacramento Bee (Nov. 29, 1991) p. B5.
H Collins (Mar. 6, 1993) Philadelphia Inquirer p. A01.
Goodchild et al., *Proc. Natl. Acad. Sci. USA* 85, 5507–5511 (1988).
Sanford, *J. Theor. Biol.* 130, 469–480 (1988).
Lisziewicz et al., *Proc. Natl. Acad. Sci. USA* 89, 11209–11213 (1992).
Stein et al *Science* (1993) 261: 1004–1012.
Agrawal (1992) "Antisense oligonucleotides as antiviral agents", *Trends in Biotechnology* 10:152–158.
Agrawal et al., "Cellular Uptake and Anti–HIV Activity of Oligonucleotides and Their Analogs", in *Gene Regulation: Biology of Antisense RNA and DNA* (Erickson and Izant, eds.) Raven Press Ltd., New York (1992) pp. 273–283.
Agrawal et al. (1992) "Synthesis and Anti–HIV Activity of Oligo–ribonucleotide and Their Phosphorothioate Analogs", *Ann. New York Acad. Sci.* (in press).
Metelev et al. (1992) "Ion Exchange High Performance Liquid Chromatography Analysis of Oligodeoxyribonucleotide Phosphorothioates", *Anal. Biochem.* 200:342–346.

(List continued on next page.)

*Primary Examiner*—Bruce R. Campbell
*Attorney, Agent, or Firm*—McDonnell Boehnen Hulbert & Berghoff

[57] ABSTRACT

Disclosed are oligonucleotides having nucleotide sequences that hybridize to at least nucleotides 324 to 348 of a conserved gag region of the HIV-1 genome. These oligonucleotides have about 25 to 30 nucleotides linked by at least one non-phosphodiester internucleotide linkage which render them resistant to nuclease digestion. Also disclosed are therapeutic formulations containing such oligonucleotides and methods of inhibition HIV-1 proliferation and of treating HIV-1 infection in a mammal.

2 Claims, 7 Drawing Sheets

OTHER PUBLICATIONS

Agrawal, "Antisense Oligonucleotides: A Possible Approach for Chemotherapy of AIDS", in *Prospects for Antisense Nucleic Acid Therapy for Cancer and AIDS*, (Wiley–Liss, Inc., New York (1991) pp. 143–158.

Agrawal et al. (1991) "Antisense oligonucleotides: gene regulation and chemotherapy of AIDS", *Adv. Drug Delviery Rev.* 6:251–270.

Harrison et al., *RNA Tumor Viruses* (Coffin et al., eds.) Cold Spring Harbor Laboratory, Cold Spring Harbor, NY (1991), pp. 235.

Matsukura et al., "A New Concept in AIDS Treatment: An Antisense Approach and Its Current Status Towards Clinical Application", in *Prospects for Antisense Nucleic Acid Therapy of Cancer and AIDS* Wiley–Liss, Inc., NY (1991) pp. 159–178.

Vickers et al. (1991) "Inhibition of HIV-LTR gene expression by oligonucleotides targeted to the TAR element", *Nucleic Acids Res.* 19:3359–3368.

Uhlmann et al. (1990) "Antisense Oligonucleotides: A New Therapeutic Principle", *Chem. Rev.* 90:543–584.

Agrawal et al. (1989) "Inhibition of human immunodeficiency virus in early infected and chronically infected cells by antisense oligodeoxynucleotides and their phosphorothioate analogues", *Proc. Natl. Acad. Sci. USA* 86:7790–7794.

Matsukura et al. (1989) "Regulation of viral expression of human immunodeficiency virus in vitro by an antisense phosphorothioate oligodeoxynucleotide against rev (art/trs) in chronically infected cells", *Proc. Natl. Acad. Sci. USA* 864244–4248.

Agrawal et al. (1988) "Oligodeoxynucleotide phosphoramidates and phosphorothioates as inhibitors of human immunodeficiency virus", *Proc. Natl. Acad. Sci. USA* 85:7079–7083.

Goodchild et al. (1988) "Inhibition of human immunodeficiency virus replication by antisense oligodeoxynucleotides", *Proc. Natl. Acad. Sci. USA* 85:5507–5511.

Matsukura et al. (1988) "Synthesis of phosphorothioate analogues of oligodeoxyribonucleotides and their antiviral activity against human immunodeficiency virus (HIV)", *Gene* 72:343–347.

Sarin et al. (1988) "Inhibition of acquired immunodeficiency syndrome virus by oligodeoxynucleoside methylphosphonates", *Proc. Natl. Acad. Sci. USA* 85:7448–7451.

van der Krol et al. (1988) "Modulation of Eukaryotic Gene Expression by Complementary RNA or DNA Sequences", *Biotech.* 6:958–976.

Sarin et al. (1987) "Inhibition of Replication of the Etiologic Agent of Acquired Immune Deficiency Syndrome (Human T–Lymphotropi Retrovirus/Lymphadenopathy–Associated Virus) by Avarol And Avarone", *J. Natl. Cancer Inst.* 78:663–666.

Wickstrom (1986) "Oligodeoxynucleotide stability in subcellular extracts and culture media", *J. Biochem. Biophys. Meth.* 13:97–102.

Zamecnik et al. (1986) "Inhibition of replication and expression of human T–cell lymphotropic virus type III in cultured cells by exogenous synthetic oligonucleotides complementary to viral RNA", *Proc. Natl. Acad. Sci. USA* 83:4143–4146.

Muesing et al. (1985) "Nucleic acid structure and expression of the human AIDS/lymphadenopathy retrovirus", *Nature* (London) 313:450–458.

Sarin et al. (1985) "Inhibition of HTLV–III/LAV Replication by Foscarnet", *Biochem. Pharmacol.* 34 4075–4079.

Uhlman Chem Review 1990 90:544–584.

Goodchild Proc Natl Acad Sci 1988 85:5507–5511.

Kinchington et al (1992) Antiviral Res 17: 53–62.

Simons et al (1992) Nature 359: 67–70.

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( i x ) FEATURE:
( A ) NAME/KEY: GEM 90
( B ) LOCATION: complementary to bp324-348 of HIV-1 DNA ( x i ) SEQUENCE DESCRIPTION: SEQ ID NO:1:

CTCTCGCACC CATCTCTCTC CTTCT                                                      2 5

( 2 ) INFORMATION FOR SEQ ID NO:2:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( i x ) FEATURE:
                ( B ) LOCATION: complementary to bp 323-348 of HIV-1 DNA ( x i ) SEQUENCE DESCRIPTION: SEQ ID NO:2:

CTCTCGCACC CATCTCTCTC CTTCTA         26

( 2 ) INFORMATION FOR SEQ ID NO:3:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( i x ) FEATURE:
                ( B ) LOCATION: complementary to bp 324-349 of HIV-1 DNA ( x i ) SEQUENCE DESCRIPTION: SEQ ID NO:3:

GCTCTCGCAC CCATCTCTCT CCTTCT         26

( 2 ) INFORMATION FOR SEQ ID NO:4:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( i x ) FEATURE:
                ( B ) LOCATION: complementary to bp 323-349 of HIV-1 DNA ( x i ) SEQUENCE DESCRIPTION: SEQ ID NO:4:

GCTCTCGCAC CCATCTCTCT CCTTCTA        27

( 2 ) INFORMATION FOR SEQ ID NO:5:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: YES ( i x ) FEATURE:
                ( B ) LOCATION: complementary to bp 322-349 of HIV-1 DNA ( x i ) SEQUENCE DESCRIPTION: SEQ ID NO:5:

GCTCTCGCAC CCATCTCTCT CCTTCTAG       28

( 2 ) INFORMATION FOR SEQ ID NO:6:

( i ) SEQUENCE CHARACTERISTICS:
                ( A ) LENGTH: 28 base pairs ( B ) TYPE: nucleic acid
                    ( C ) STRANDEDNESS: single
                    ( D ) TOPOLOGY: linear ( i i ) MOLECULE TYPE: cDNA ( i i i ) HYPOTHETICAL: NO ( i v ) ANTI-SENSE: YES ( i x ) FEATURE:
                    ( B ) LOCATION: complementary to bp 323-350 of HIV-1 DNA ( x i ) SEQUENCE DESCRIPTION: SEQ ID NO:6:

CGCTCTCGCA CCCATCTCTC TCCTTCTA                                                                    28

( 2 ) INFORMATION FOR SEQ ID NO:7:

( i ) SEQUENCE CHARACTERISTICS:
                    ( A ) LENGTH: 29 base pairs
                    ( B ) TYPE: nucleic acid
                    ( C ) STRANDEDNESS: single
                    ( D ) TOPOLOGY: linear ( i i ) MOLECULE TYPE: cDNA ( i i i ) HYPOTHETICAL: NO ( i v ) ANTI-SENSE: YES ( i x ) FEATURE:
                    ( B ) LOCATION: complementary to bp 322-350 of HIV-1 DNA ( x i ) SEQUENCE DESCRIPTION: SEQ ID NO:7:

CGCTCTCGCA CCCATCTCTC TCCTTCTAG                                                                   29

( 2 ) INFORMATION FOR SEQ ID NO:8:

( i ) SEQUENCE CHARACTERISTICS:
                    ( A ) LENGTH: 30 base pairs
                    ( B ) TYPE: nucleic acid
                    ( C ) STRANDEDNESS: single
                    ( D ) TOPOLOGY: linear ( i i ) MOLECULE TYPE: cDNA ( i i i ) HYPOTHETICAL: NO ( i v ) ANTI-SENSE: YES ( i x ) FEATURE:
                    ( B ) LOCATION: complementary to bp 321-350 of HIV-1 DNA ( x i ) SEQUENCE DESCRIPTION: SEQ ID NO:8:

CGCTCTCGCA CCCATCTCTC TCCTTCTAGC                                                                  30

( 2 ) INFORMATION FOR SEQ ID NO:9:

( i ) SEQUENCE CHARACTERISTICS:
                    ( A ) LENGTH: 30 base pairs
                    ( B ) TYPE: nucleic acid
                    ( C ) STRANDEDNESS: single
                    ( D ) TOPOLOGY: linear ( i i ) MOLECULE TYPE: cDNA ( i i i ) HYPOTHETICAL: NO ( i v ) ANTI-SENSE: YES ( i x ) FEATURE:
                    ( B ) LOCATION: complementary to bp 322-351 of HIV-1 DNA ( x i ) SEQUENCE DESCRIPTION: SEQ ID NO:9:

ACGCTCTCGC ACCCATCTCT CTCCTTCTAG                                                                30

( 2 ) INFORMATION FOR SEQ ID NO:10:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear       ( i i ) MOLECULE TYPE: cDNA       ( i i i ) HYPOTHETICAL: NO       ( i v ) ANTI-SENSE: YES       ( i x ) FEATURE:
          ( A ) NAME/KEY: GEM 90
          ( B ) LOCATION: complementary to bp 327-346 of HIV-1 DNA       ( x i ) SEQUENCE DESCRIPTION: SEQ ID NO:10:

CTCGCACCCA TCTCTCTCCT                                                                           20

( 2 ) INFORMATION FOR SEQ ID NO:11:

( i ) SEQUENCE CHARACTERISTICS:
          ( A ) LENGTH: 70 base pairs
          ( B ) TYPE: nucleic acid
          ( C ) STRANDEDNESS: single
          ( D ) TOPOLOGY: linear       ( i i ) MOLECULE TYPE: cDNA to genomic RNA       ( i i i ) HYPOTHETICAL: NO       ( i v ) ANTI-SENSE: NO       ( v i ) ORIGINAL SOURCE: HIV-1

( v i i i ) POSITION IN GENOME: 311-380

( x i ) SEQUENCE DESCRIPTION: SEQ ID NO:11:

ACTAGCGGAG GCTAGAAGGA GAGAGATGGG TGCGAGAGCG                                                      40

TCAGTATTAA GCGGGGGAGA ATTAGATCGA                                                                 70

( 2 ) INFORMATION FOR SEQ ID NO:12:

( i ) SEQUENCE CHARACTERISTICS:
          ( A ) LENGTH: 41 base pairs
          ( B ) TYPE: nucleic acid
          ( C ) STRANDEDNESS: single
          ( D ) TOPOLOGY: linear       ( i i i ) HYPOTHETICAL: NO       ( i v ) ANTI-SENSE: NO       ( x i ) SEQUENCE DESCRIPTION: SEQ ID NO:12:

CGGAGGCTAG AAGGAGAGAG ATGGGTGCGA GAGCGTCAGT A                                                    41

( 2 ) INFORMATION FOR SEQ ID NO:13:

( i ) SEQUENCE CHARACTERISTICS:
          ( A ) LENGTH: 51 base pairs
          ( B ) TYPE: nucleic acid
          ( C ) STRANDEDNESS: single
          ( D ) TOPOLOGY: linear       ( i i i ) HYPOTHETICAL: NO       ( i v ) ANTI-SENSE: NO -continued ( x i ) SEQUENCE DESCRIPTION: SEQ ID NO:13:

GACTAGCGGA GGCTAGAAGG AGAGAGATGG GTGCGAGAGC GTCAGTATTA A    51

( 2 ) INFORMATION FOR SEQ ID NO:14:

( i ) SEQUENCE CHARACTERISTICS:
    ( A ) LENGTH: 58 base pairs
    ( B ) TYPE: nucleic acid
    ( C ) STRANDEDNESS: single
    ( D ) TOPOLOGY: linear   ( i i i ) HYPOTHETICAL: NO   ( i v ) ANTI-SENSE: NO   ( x i ) SEQUENCE DESCRIPTION: SEQ ID NO:14:

GACTAGCGGA GGCTAGAAGG AGAGAGATGG GTGCGAGAGC GTCAGTATTA AGCGGGGG    58

( 2 ) INFORMATION FOR SEQ ID NO:15:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear   ( i i i ) HYPOTHETICAL: NO   ( i v ) ANTI-SENSE: YES   ( x i ) SEQUENCE DESCRIPTION: SEQ ID NO:15:

CGCTTAATAC TGACGCTCTC GCACCCAT    28

THERAPEUTIC ANTI-HIV ANTI-VIRAL OLIGONUCLEOTIDES AND PHARMACEUTICAL FORMULATIONS THEREOF

This application is a continuation of application Ser. No. 07/958,135, filed Oct. 5, 1992, now abandoned.

FIELD OF THE INVENTION

This invention relates to the treatment of HIV-1 infection. More particularly, this invention relates to chemotherapeutic agents called antisense oligonucleotides and to pharmaceutical compositions containing such oligonucleotides. This invention also relates to methods of inhibiting HIV replication and treating HIV-1 infection using such antisense oligonucleotides.

BACKGROUND OF THE INVENTION

Human T-cell leukemia lymphotropic virus-type III (HTLV-III), now more commonly known as human immunodeficiency virus type 1 (HIV-1), is thought to be the etiological agent of acquired immune deficiency syndrome (AIDS). This virus is part of the Retroviridaie family, the members of which contain an RNA genome and reverse transcriptase activity. During their growth cycle, retroviruses copy their RNA into proviral DNA. The proviral DNA is able to integrate into the chromosomal DNA of the host cell where it uses the transcriptional and translational machinery of the host to express viral RNA and proteins. Viruses are released from the cell by budding from the cytoplasmic membrane. In the case of HIV-1, viral replication results in the death of helper T-cell host cells, which leads to a state of severe immunodeficiency, to the development of various malignancies and opportunistic infections, and ultimately to the death of the infected organism.

The incidence of AIDS has risen to epidemic proportions in many countries without the development of preventative treatments or therapies which are successful in the long term. Those few therapeutic agents which have been prescribed, such as the nucleoside analogs 3'-azido-3'-deoxythymidine (AZT), dideoxyinosine (ddI), and dideoxycytosine (ddC), have met with limited success. This has been in part because of the cytotoxicity of these agents. In addition, some viruses escape due to mutations that render them insensitive to these agents and the difficulty of antiviral action due to the ability of the virus to integrate into the host's genome. Thus, there is a long felt need for more effective therapeutic agents and preventative therapies for AIDS.

Recently new chemotherapeutic agents have been developed which are capable of modulating cellular and foreign gene expression. These agents, called antisense oligonucleotides, bind to a target single-stranded nucleic acid molecules according to the Watson-Crick or the Hoogstein rule of base pairing, and in doing so, disrupt the function of the target by one of several mechanisms: by preventing the binding of factors required for normal translation or transcription; in the case of an mRNA target, by triggering the enzymatic destruction of the message by RNase H; or by destroying the target via reactive groups attached directly to the antisense oligonucleotide.

Antisense oligodeoxynucleotides have been designed to specifically inhibit the expression of HIV-1 and other viruses (see, e.g., Agrawal (1992) *Trends in Biotechnology* 10:152–158; Agrawal et al. in *Gene Regulation: Biology of Antisense RNA and DNA* (Erickson and Izant, eds.) Raven Press Ltd., New York (1992) pp. 273–283); Matsukura et al. in *Prospects for Antisense Nucleic Acid Therapy of Cancer and AIDS*, Wiley-Liss, Inc. (1992) pp. 159–178; and Agrawal (1991) in *Prospects for Antisense Nucleic Acid Therapy for Cancer and AIDS*, (Wickstrom, ed.) Liss, New York, pp. 145–148). For example, it has been shown that antisense oligonucleotides having unmodified phosphodiester internucleoside bonds and sequences complementary to portions of genomic HIV-1 ribonucleic acid (RNA) inhibit viral replication in early infected cells (Zamecnik et al. (1986) *Proc. Acid. Sci. U.S.A.* 83:4143–4147; Goodchild et al. (1988) *Proc. Natl. Acad. Sci U.S.A.* 85:5507–5511). However, these molecules are less able to inhibit viral replication in chronically infected cells (Agrawal et al. (1989) *Proc. Natl. Acad. Sci U.S.A.* 86:7790–7794), mainly because of their nuclease susceptibility (Wickstrom (1986) *J. Biochem. Biophys. Meth.* 13:97–102). Therefore, chemically modified, nuclease-resistant analogs have been developed which are effective in inhibiting HIV-1 replication in tissue cultures (Sarin et al. (1988) *Proc. Nail Acad. Sci. U.S.A.* 85:7448–7451; Agrawal et al. (1988) *Proc. Natl Acad. Sci. U.S.A.* 85:7079–7083; Matsukura et al. (1988) *Gene* 72:343–347). These analogs include oligonucleotides with nuclease-resistant phosphorothioate internucleotide linkages shown to inhibit HIV-1 replication in both acute infection (Agrawal et al. (1989) *Proc. Natl. Acad. Sci U.S.A.* 86:7790–7794) and in chronically infected cell lines (Agrawal et al. (1991) in *Gene Regulation: Biology of Antisense RNA*, eds. Erickson et al. (Raven Press, New York), pp. 273–284; Vickers et al. (1991) *Nucleic Acids Res.* 19:3359–3368; Matsukura et al. (1989) *Proc. Natl Acad. Sci.* 86:4244–4248; Agrawal et al. (1988) *Proc. Natl Acad. Sci. U.S.A.* 85:7079–7083). However, there still remains a need for a more effective anti-HIV oligonucleotide having therapeutic effects that are accompanied by low or no cellular toxicity.

SUMMARY OF THE INVENTION

Novel chemotherapeutic agents have been designed which inhibit HIV-1 replication. These agents are synthetic oligonucleotides having non-phosphodiester internucleotide linkages and a nucleotide sequence that is complementary to a portion of the conserved gag region of the HIV-1 genome. Gag is part of the structural gene of HIV-1 which is common to all, retroviruses. Sequences situated around the gag initiation codon are known to be essential for viral packaging. The antisense oligonucleotide agent acts by binding to the target DNA or RNA, thereby inhibiting initiation of DNA replication and DNA expression, and inhibiting viral packaging by disrupting the secondary structure of its DNA.

Oligonucleotides of the invention are more specific, less toxic, and have greater nuclease resistance than many other chemotherapeutic agents designed to inhibit HIV-1 replication. In particular, compounds according to the invention having non-phosphodiester linkages are more resistant to nucleolytic degradation than are compounds having solely phosphodiester linkages. In addition, they are more active in inhibiting viral replication than other known antisense oligonucleotides containing a nucleotide sequence complementary to less than the 324 to 348 HIV-1 gag sequence.

In its broadest aspects, the invention features an antisense oligonucleotide having a nucleotide sequence of 25 to 30 nucleotides that hybridizes to at least nucleotides 324 to 348 of the gag region of HIV-1. In one preferred embodiment of the invention, the oligonucleotides also have at least one phosphorothioate internucleotide linkage. Such phosphorothioate linkages contain a substitution of sulfur for oxygen, thereby rendering the oligonucleotide resistant to nucleolytic degradation.

Another embodiment of the invention is an oligonucleotide having twenty-five nucleotides linked by at least one phosphorothioate internucleotide linkage. This oligonucleotide is referred to as a "25 mer." The nucleotide sequence of this 25 mer is set forth in the Sequence Listing as SEQ ID NO:1. Other embodiments of the invention include phosphorothioate oligonucleotides having 26, 27, 28, 29, or 30 nucleotides, the sequences of which are complementary to nucleotides 324–348 of HIV-1 in addition to other flanking nucleotides. The sequences of two preferred 26 mers are set forth in the Sequence Listing as SEQ ID NOS:2 and 3; that of a preferred 27 mer are found in SEQ ID NO:4; those of preferred 28 mers are found in SEQ ID NOS:5 and 6; that of a preferred 29 mer is set forth in SEQ ID NO:7; and those of preferred 30 mers are found in SEQ ID NOS:8 and 9.

The invention also provides therapeutic formulations including an oligonucleotide described above in a physiologically acceptable carrier, and methods of inhibiting the proliferation of HIV-1 and of treating HIV-1 infection in a mammal using these formulations.

BRIEF DESCRIPTION OF THE DRAWING

The foregoing and other objects of this invention, the various features thereof, as well as the invention itself, may be more fully understood from the following description, when read together with the accompanying drawings, in which.

DETAILED DESCRIPTION OF THE PREFERRED EMBODIMENTS

Disclosed are antisense oligodeoxynucleotides with non-phosphodiester internucleotide linkage which are particularly active in inhibiting the replication of HIV-1, and which are more resistant to nuclease digestion than oligonucleotides with phosphodiester internucleotide linkages, and which are less cytotoxic than other anti-HIV chemotherapeutic agents. These oligonucleotides (SEQ ID NOS:1–9) are targeted to the region around the gag initiation codon of the HIV-1 genome. Sequences situated in this region have been demonstrated to be essential for viral packaging. These sequences form a stable secondary structure (Harrison et al. (1991) in RNA Tumor Viruses (Coffin et al., eds.) Cold Spring Harbor Laboratory, Cold Spring Harbor, N.Y., pp. 235). The oligonucleotides of the invention have been designed to bind to this region, thereby disrupting its natural stability and resulting ultimately in the inhibition of viral packaging and translation of gag mRNA.

Figure 1:
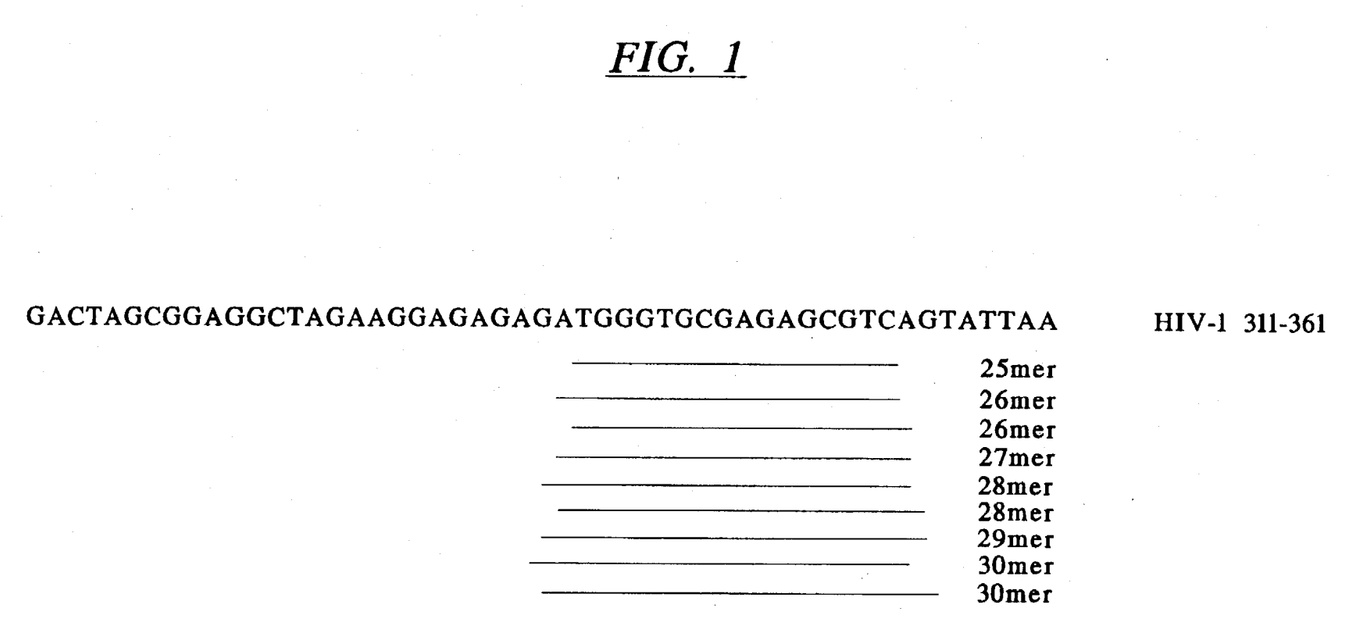
FIG. 1. is a schematic representation of the targeted gag initiation region of the HIV-1 genome (SEQ ID NO:13) and the complementarity thereto of antisense phosphorothioate nucleotides of the invention.
Figure 2:
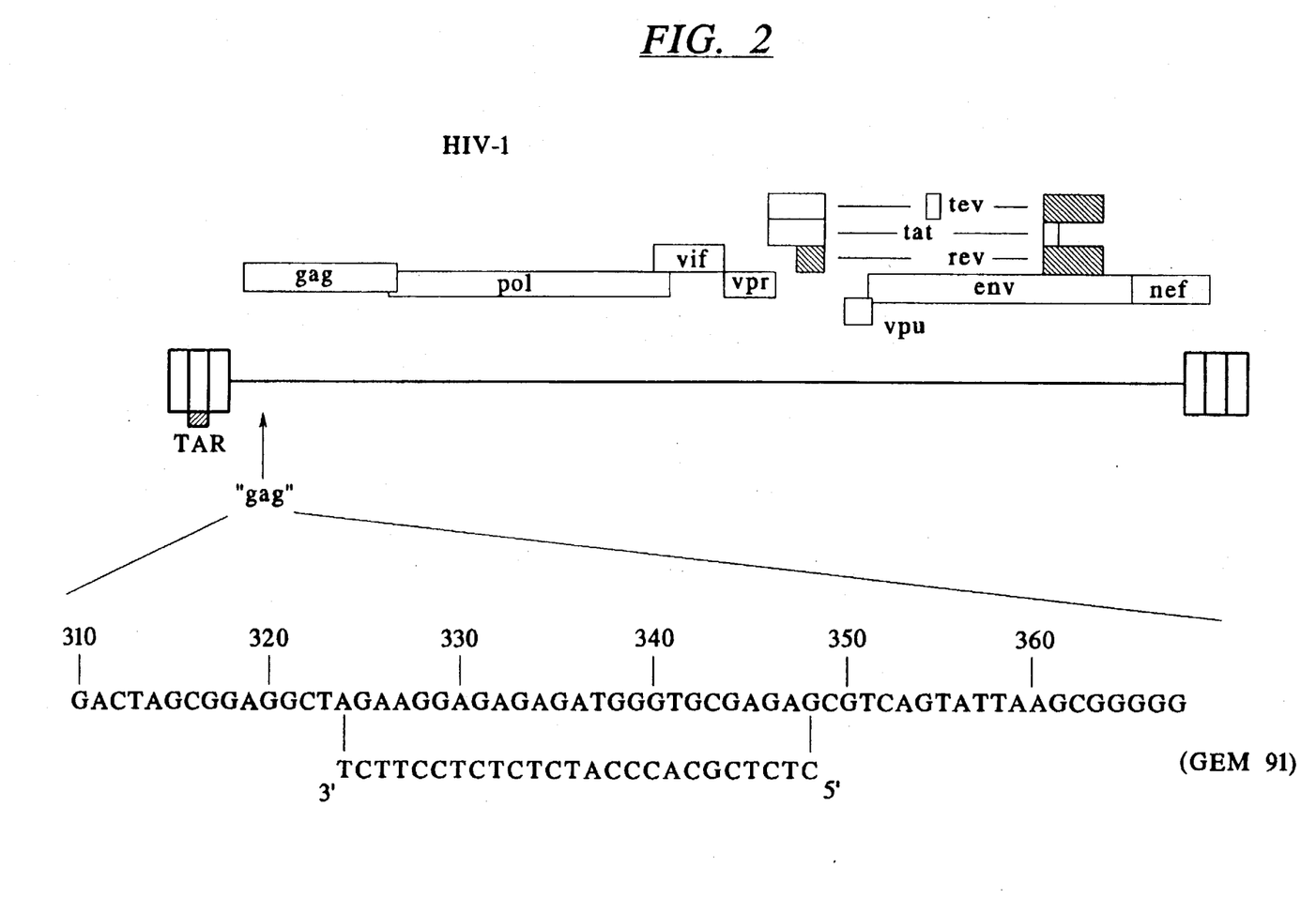
FIG. 2. is a schematic representation of the targeted gag initiation region (SEQ ID NO:14) and the 25 mer of the invention (SEQ ID NO:1)

The oligonucleotides are complementary to at least sequence 324–348 of the gag region (SEQ ID NO:11) of HIV-1 (FIG. 2) (Muessing et al. (1985) Nature (London) 313:450–458). Sequence 324–348 is very conserved among strains of HIV-1, as shown below in TABLE 1.

TABLE 1

| Sequence of: | |
|---|---|
| 324–348 → | TCTTCCTCTCTCTACCCACGCTCTC SEQ ID NO: 1 |
| CONSENSUS → | CGGAGGCTAGAAGGAGAGAGATGGGTGCGAGAGCGTCAGTA SEQ ID NO: 12 |

| Strains of HIV-1 | | |
|---|---|---|
| HTLV3/LLAV | G | A |
| HIVLAI | G | A |
| HIVNL43 | G | G |
| HIVMN | G | G |
| HIVJH3 | G | A |
| HIVOYI | G | A |
| HIVCDC4 | G | A |
| HIVRF | G | A |
| HIVMAL | G | A (African) |

TABLE 1-continued

| | | | |
|---|---|---|---|
| HIVU455 | | A | A CCTCAG (Ugandan) |
| HIVSF2 | (GA) 4G | | G |
| HIVNDK | | G | A |

Targeting an antisense oligonucleotide to such a conserved region including an active gene allows for efficient inhibition of HIV proliferation without the generation of "escape mutants." Escape mutants arise when a mutation occurs in a region of the genome targeted by the antisense oligonucleotide. They occur at a higher frequency in non-coding regions (like the SA region of HIV-1) than in regions encoding a protein.

The nucleotide sequences of the oligonucleotides of the invention each are complementary to at least nucleotides 324–348 of the HIV-1 genome. One aspect of the invention is an oligonucleotide consisting essentially of this sequence and is referred to herein as a 25 mer. The sequence of the 25 mer is set forth in the Sequence Listing as SEQ ID NO:1. Other claimed oligonucleotides with the ability to inhibit HIV-1 replication contain the sequence of the 25 mer flanked in the 3' and/or 5' direction by additional nucleotides complementary to nucleotides flanking the 324 to 348 region of HIV-1. The sequence of these oligonucleotides is set forth in TABLE 2 and in the Sequence Listing as SEQ ID NOS:2–9. Also listed for comparison is the sequence of a 20 mer, (Agrawal et al. (1992) *Gene Regulation: Biology of Antisense DNA and RNA* (Erickson and Izant, eds.) Raven Press, Ltd., New York, pp 273–283 (SEQ ID NO:10).

nucleotides of the invention include 3' terminal sequences which are internally complementary to each other, thereby forming a double stranded loop at the end of the structure. Of course other modifications of the oligonucleotides enhancing nuclease resistance, specificity, activity, and decreasing cytotoxicity, may also be performed.

The oligonucleotides of the invention can be synthesized by various known procedures including solid phase methods using phosphoramidite or H-phosphonate chemistry (see. e.g., Agrawal et al. (1992) *Ann. New York Acad. Sci.* (in press); Agrawal (1991) *TIBTECH* 10:152–158), and can be purified by known reversed phase or ion exchange HPLC or hybridization affinity chromatographic methods (see, e.g., Metelev and Agrawal (1992) *Anal. Biochem.* 200:342–346).

Studies of the mechanism and efficiency of antisense oligonucleotides in inhibiting viral replication can be approached effectively in several in vitro systems. One system uses chronically infected human T lymphocytes such as CEM cells. In such a system the infected cells are cultured in the absence and presence of different concentrations of the antisense oligonucleotide of the invention for varying lengths of time. Unlike the oligonucleotides of the invention, nucleotide analogs such as AZT, ddI, and ddC do not inhibit HIV replication in this system.

TABLE 2

| Oligonucleotide | Sequence | SEQ ID No. |
|---|---|---|
| 25mer | 5'-CTCTCGCACCCATCTCTCTCCTTCT-3' | 1 |
| 26mer | CTCTCGCACCCATCTCTCTCCTTCTA | 2 |
| 26mer | GCTCTCGCACCCATCTCTCTCCTTCT | 3 |
| 27mer | GCTCTCGCACCCATCTCTCTCCTTCTA | 4 |
| 28mer | GCTCTCGCACCCATCTCTCTCCTTCTAG | 5 |
| 28mer | CGCTCTCGCACCCATCTCTCTCCTTCTA | 6 |
| 29mer | CGCTCTCGCACCCATCTCTCTCCTTCTAGC | 7 |
| 30mer | ACGCTCTCGCACCCATCTCTCTCCTTCTAG | 8 |
| 30mer | ACGCTCTCGCACCCATCTCTCTCCTTCTAGC | 9 |
| 20mer | TCCTCTCTCTACCCACGCTC | 10 |

Modified oligonucleotides of the invention are also useful inhibitors of HIV-1 proliferation, including those with artificial internucleotide linkages other than phosphorothioate linkages. Other known artificial linkages include methyl phosphonates, phosphoramidates, dithioates, bridged phosphorothioates, bridge phosphoramidates, sulfones, sulfates, ketos, phosphate esters, and phosphorbutylamines (see, e.g., van der Krol et al. (1988) *Biotech.* 6:958–976; and Uhlmann et al. (1990) *Chem. Rev.* 90:543–585). In addition, phosphorothioates and other artificial oligonucleotides having additional structures which confer nuclease resistance are also useful, such as capped 3' and/or 5' ends (see, e.g., U.S. patent application Ser. No. 07/698,568; Letsinger et al. (1989) *Biochem.* 86:6553–6556; and Reed et al. (1991) *Bioconjugate Chem.* 2:217–225) and chimeric oligonucleotides (see U.S. Pat. No. 5,149,797, as well as hybrid oligonucleotides having regions of RNA and DNA). Other modifications conferring nuclease resistance to the oligo- However, because chronically infected cells are CD4−, reinfection cannot occur. Thus, such an in vitro culture does not parallel the in vitro conditions present in an HIV-infected person, where only a small percentage of their CD4+ cells are infected and producing virus. A model for drug studies which more closely approaches in vivo condition is a cell culture with an acute, low multiplicity of infection (MOI). In this system only a fraction of the cell population harbors virus while the other cell are uninfected and are CD4+. Human T cell lines such as CEM or H9 (ATCC HTB 176) are infected with HIV for one to several hours and then cultured in the absence or presence of varying concentrations of oligonucleotide for different period of time.

The ability of the oligonucleotides to inhibit HIV-1 replication can be measured by determining the level of HIV expression and the cytotoxic effect of the oligonucleotides on the infected cells. HIV expression can be monitored by a number of parameters, including syncytia formation, p24 expression, p17 expression, and reverse transcriptase activity (see Agrawal et al (1991) *Adv. Drug Delivery Rev.* 6:251–270; Sarin et al. (1985) *Biochem. Pharmacol.* 34:4075–4079; and Sarin et al. (1987) *J. Natl. Cancer Inst.* 78:663–666). The inhibition of viral cryopathic effect (CPE) by the oligonucleotides can be studied by the MTT or trypan blue exclusion method.

The oligonucleotides of the invention may be used to inhibit the proliferation of HIV-1 in infected cells. In this method, a therapeutic formulation including an antisense oligonucleotide of the invention is provided in a physiologically acceptable carrier. HIV-1 infected cells are then treated with the therapeutic formulation in an amount sufficient to enable the binding of the oligonucleotide to the gag region of HIV-1 proviral DNA and or mRNA in the infected cells. In this way, the binding of the oligonucleotide to the HIV-1 DNA or mRNA inhibits the expression and replication of the virus.

The oligonucleotides of the invention may also be used to treat HIV-1 infection in mammals. In this method, a therapeutic formulation including an antisense oligonucleotide of the invention is provided in a physiologically acceptable carrier. The mammal is then treated with the therapeutic formulation in an amount sufficient to enable the binding of the oligonucleotide to the gag region of HIV-1 proviral DNA and/or mRNA in the infected cells. In this way, the binding of the oligonucleotide inhibits HIV-1 DNA expression and replication of the virus.

As used herein, a "physiologically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Effective dosages of the oligonucleotide and modes of its administration in the treatment of AIDS can be determined by routine experimentation. The pharmaceutical forms suitable for injectable use include sterile aqueous solutions or dispersions and sterile powders for the extemporaneous preparation of sterile injectable solutions or dispersions. In all cases the form must be sterile. It must be stable under the conditions of manufacture and storage and may be preserved against the contaminating action of microorganisms, such as bacterial and fungi. The carrier can be a solvent or dispersion medium. The prevention of the action of microorganisms can be brought about by various antibacterial and antifungal agents. Prolonged absorption of the injectable therapeutic agents can be brought about by the use of the compositions of agents delaying absorption.

The oligonucleotide in the carrier may be administered by intravenous or intraperitoneal injection, or by intranasal, oral, transdermal, or subcutaneous administration.

Sterile injectable solutions are prepared by incorporating the oligonucleotide in the required amount in the appropriate solvent, followed by filtered sterilization.

HIV has a high mutational rate and therefore all drugs designed to treat virus infection, including antisense oligonucleotides, may induce the formation of escape mutants. To overcome this problem, combination chemotherapy has been suggested for treatment of HIV-infected patients. This therapy involves more than one drug directed against different targets, such as reverse transcriptase inhibitors combined with protease inhibitors. Alternatively, antisense treatment targeting different sequences either in combination or in sequential treatment schedules can be administered, resulting in different selection pressures on the virus with little time to develop escape mutants. Accordingly, the first treatments consist of a mixture of oligonucleotides of the invention, followed by sequential administration of oligonucleotides targeted to other conserved regions of the HIV-1 genome.

The invention will be further understood from the following non-limiting examples.

EXAMPLE 1

Synthesis of the Oligodeoxynucleotide Phosphorothioates

Phosphorothioate-modified oligodeoxynucleotides are synthesized using H-phosphonate chemistry on an automated synthesizer (Millipore 8700, Bedford, Mass.) on a 5 to 10 mmole scale. After the assembly of the required sequence, the CPG-bound oligonucleotide H-phosphonate is oxidized with sulphur in pyridine/triethylamine/carbon disulfide to generate phosphorothiote linkages. The deprotection is completed in concentrated ammonia at 40° C. for 48 hr. Purification is carried out by preparative reverse-phase chromatography followed by ion exchange chromatography. Finally, purified oligonucleotides are dialyzed against water and lyophilized. Oligonucleotide phosphorothioates are checked for their purity by HPLC and PAGE (Agrawal et al. (1989) *Proc. Natl. Acad. Sci U.S.A.* 86:7790–7794).

The oligonucleotide used for comparison in these experiments is the phosphorothioate 20 mer, whose nucleotide sequence (SEQ ID NO:10) is complementary to a portion of the gag region (nucleotides numbers 327–346) of the HIV-1 genome (see SEQ ID NO:11). Like the oligonucleotides of the invention, this 20 mer has phosphorothioate internucleotide linkages. However, as shown in the experiments described in the exemplification which follows, it has less HIV-1 inhibitory activity than the oligonucleotides of the invention.

EXAMPLE 2

Specificity of Antisense and Control Oligonucleotides

To determine the specificity of the antisense oligonucleotides, their biological effect may be compared to the same sized oligonucleotide which is not complementary to any known cellular or viral genes. Three such nonspecific control oligonucleotides are chosen, of which one having a "random" sequence is theoretically the best. The random sequence is synthesized as a degenerate oligonucleotide, by coupling a mixture of four nucleotides at each stage (theoretically it contains $4^{28}=7.2\times10^{16}$ sequences), and thus measures the extent of sequence nonspecific inhibition.

EXAMPLE 3

HIV-1 Inhibition Assays

The following assays were used to measure the ability of the oligonucleotide of the invention to inhibit HIV-1 replication.

A. Syncytia Assay

The ability of the oligonucleotides of the invention to inhibit HIV-1 replication, and thus syncytia formation, in tissue culture is tested in T cell cultures according to the method of Agrawal and Sarin (1991, ibid.) Briefly, CEM cells are infected with HIV-1 virions (0.01–0.1 TCID$_{50}$/cell) for one hour at 37° C. After one hour, unadsorbed virions are washed and the infected cells are divided among wells of 24 well plates. To the infected cells, an appropriate concentration (from stock solution) of oligonucleotide is added to obtain the required concentration in 2 ml medium. The cells are then cultured for three days. At the end of three days, infected cells are examined visually for syncytium formation or stained with trypan blue or CTT for cytopathic effect determination.

B. p24 Expression Assay

HIV expression can be determined by measuring the level of viral protein p24 expression in CEM cells essentially as described by Agrawal and Sarin (*Adv. Drug Delivery Rev.* (1991) 6:251–270). Briefly, cells are pelleted and the resuspended in phosphate saline at a concentration of about $10^6$/ml. The cells are spotted on toxoplasmosis slides, air dried, and fixed in methanol/acetone (1:1) for 15 min at room temperature (RT). The slides are next incubated with 10% normal goat serum at RT for 30 min and washed with phosphate buffered saline (PBS). Anti-p24 monoclonal antibody is added to each well, and the slides are incubated in a humid chamber at 37° C. The slides are labelled with goat anti-mouse IgG for 30 min and then washed in PBS overnight. The percentage of cells fluorescing in oligonucleotide-treated and untreated cells is compared.

C. Cytopathic Effect (CPE)

HIV-induced cytopathic effect is determined by measuring the decrease in the number of viable cells after infection. The cells are counted by adding MTT or trypan blue dye to the cells and determining how may cells (dead) take up the dye. The assay is done in triplicate.

D. Reverse Transcriptase Assay

This assay is performed essentially as described in Agrawal et al. (*Adv. Drug Delivery Rev.* (1991) 6:251–270). Supernatants from virus-infected cultures in the presence and absence of oligonucleotide are collected and virus particles precipitated with poly(ethyleneglycol). The virus pellet is suspended in 300 µl of buffer containing 50 mM Tris-HCl (pH 6.8), 5 mM dithiothreitol (DTT), 250 mM KCl, and 25% Triton X-100. Reverse transcriptase actiovity in the solubilized pellet is assayed in a 50µl reaction mixture containing 50 mM Tris-HCl (pH 7.8), 5 mM DTT, 100 mM KCl, 0.01% Triton X-100, 5 µg dt15.rAn as template primer, 10 mM MgCl2, 15 µM [$^3$H]dTTP (15 Ci/mmol), and 10 µl of the disrupted virus suspension. After incubation for 1 hr at 37° C. and subsequent addition of 50 µg yeast tRNA, the incorporation into the cold trichloroacetic acid-insoluble DNA fraction is assayed by counting in a β scintillation counter.

EXAMPLE 4

Inhibition of HIV-1 Replication by a 25 mer in vitro

The ability of the antisense oligonucleotides of the invention to inhibit HIV-1 infection in a number of established cell lines can be established by performing the short term (acute infection) and long term assays described below.

A. Short Term (acute infection) Assays

1. In CEM Cells

CEM cells ($5\times10^4$ cells/ml) are infected with HIV-1 (HTLV IIIB strain) for 4 hours at 37° C. Infected and uninfected cells are then cultured in the presence and absence of oligonucleotide such as 25 mer or a control oligonucleotide that has no activity (e.g., a 20 mer with SEQ ID NO:10) for up to 6 days at 37° C. (in triplicate). The concentrations at which the 25 mer is tested are 0.32 µg/ml (0.05 µM), 1.00 µg/ml (0.2 µM), 3.2 µg/ml (0.04 µM), 10 µg/ml (1.5 µM), 32 µg/ml (4 µM), and 100 µg/ml (10.5 µM). The effective concentration to cause 50% inhibition of virus replication (EC$_{50}$) is determined graphically. After the experiment the level of HIV-1 expression is measured by the syncytia formation assay (TABLE 3A) and the p24 expression assay (TABLE 3B). Cytotoxicity is measured by colorimetric analysis after addition of MTT to wells as described above (TABLE 3C).

TABLE 3A

Syncytia Inhibition Assay

| Oligo-nucleotide | Conc. µg/ml | Avg. #* Syncytia | % Inhib. Syncytia | Reduct. (%) | EC$_{50}$ µg/ml |
|---|---|---|---|---|---|
| 20mer | 0.32 | 147 | 0 | 4 | 1.81 |
|  | 1.00 | 153 | 0 | 0 |  |
|  | 3.2 | 0 | 100 | 98 |  |
|  | 10 | 0 | 100 | 100 |  |
|  | 32 | 0 | 100 | 100 |  |
|  | 100 | 0 | 100 | 100 |  |
| 25mer | 0.32 | 145 | 6 | 6 | 1.41 |
|  | 1.00 | 108 | 30 | 29 |  |
|  | 3.2 | 0 | 100 | 100 |  |
|  | 10 | 0 | 100 | 100 |  |
|  | 32 | 0 | 100 | 100 |  |
|  | 100 | 0 | 100 | 100 |  |

*Average number of syncytia formed in control (infeected but untreated cells) was 153.

These results demonstrate that an oligonucleotide of the invention, the 25 mer, partially inhibits (30%) syncytia formation at a lower concentration (1.00 g/ml) than does the 20 mer. In addition, the effective concentration of oligonucleotide to cause inhibition of virus replication (EC$_{50}$) was lower for the 25 mer than for 20 mer, indicating that the 25 mer has more activity.

TABLE 3B

HIV p24 Antigen Assay

| Oligo-nucleotide | Conc. µg/ml | p24 expression % of virus control | Reduct. of p24 expression (%) |
|---|---|---|---|
| 20mer | 0.32 | 133 | — |
|  | 1.00 | 114 | — |
|  | 3.20 | 93 | 7 |
|  | 10 | 44 | 56 |
|  | 32 | 53 | 47 |
|  | 100 | 62 | 38 |
| 25mer | 0.32 | 115 | — |
|  | 1.00 | 115 | — |
|  | 3.20 | 57 | 46 |
|  | 10.00 | 59 | 41 |
|  | 32 | 43 | 57 |
|  | 100 | 35 | 65 |

The 25 mer was able to reduce p24 expression by nearly 50% at a lower concentration than was the 20 mer.

Furthermore, at high concentrations (100 µg/ml) the 25 mer was nearly twice as effective in reducing p24 expression as the 20 mer, indicating that it is highly active in inhibiting HIV-1 expression.

TABLE 3C

HIV Cytopathic Assay

| Oligo. nucleotide | Conc. µg/ml | Reduction in viral cytopathic effect (%) | $EC_{50}$ |
|---|---|---|---|
| Experiment 1 | | | |
| 20mer | 0.32 | 0 | 7.75 |
| | 1.00 | 6 | |
| | 3.2 | 28 | |
| | 10.0 | 62 | |
| | 32.0 | 84 | |
| | 100 | 87 | |
| 25mer | 0.32 | 4 | 2.54 |
| | 1.00 | 26 | |
| | 3.2 | 56 | |
| | 10.0 | 87 | |
| | 32.0 | 95 | |
| | 100 | 87 | |

| Oligo. nucleotide | Conc. µg/ml | Reduction in viral cytopathic effect (%) | $EC_{50}$ |
|---|---|---|---|
| Experiment 2 | | | |
| 20mer | 0.32 | 0 | 3.91 |
| | 1.00 | 0 | |
| | 3.2 | 41 | |
| | 10.0 | 100 | |
| | 32.0 | 100 | |
| | 100 | 100 | |
| 25mer | 0.30 | 0 | |
| | 1.00 | 0 | |
| | 3.2 | 70 | |
| | 10.0 | 100 | |
| | 32.2 | 100 | |
| | 100 | 100 | |

| Oligo. nucleotide | Conc. µg/ml | Reduction in viral cytopathic effect (%) | $EC_{25}$ | $EC_{50}$ | $EC_{90}$ |
|---|---|---|---|---|---|
| Experiment 3 | | | | | |
| 20mer | .32 | 6 | 1.36 | 1.84 | 3.20 |
| | 1.00 | 0 | | | |
| | 3.2 | 95 | | | |
| | 10.0 | 100 | | | |
| | 32.0 | 100 | | | |
| | 100 | 100 | | | |
| 25mer | 0.32 | 0 | 1.29 | 1.75 | 3.01 |
| | 1.00 | 4 | | | |
| | 3.2 | 100 | | | |
| | 10.0 | 100 | | | |
| | 32.0 | 100 | | | |
| | 100 | 100 | | | |

The $EC_{50}$ of the 25 mer required to reduce viral cytopathic effect was significantly lower than that of the 20 mer in each of three experiments performed, indicating that it has less cytoxicity than 20 mer.

2. In H9 Cells

Figure 5:
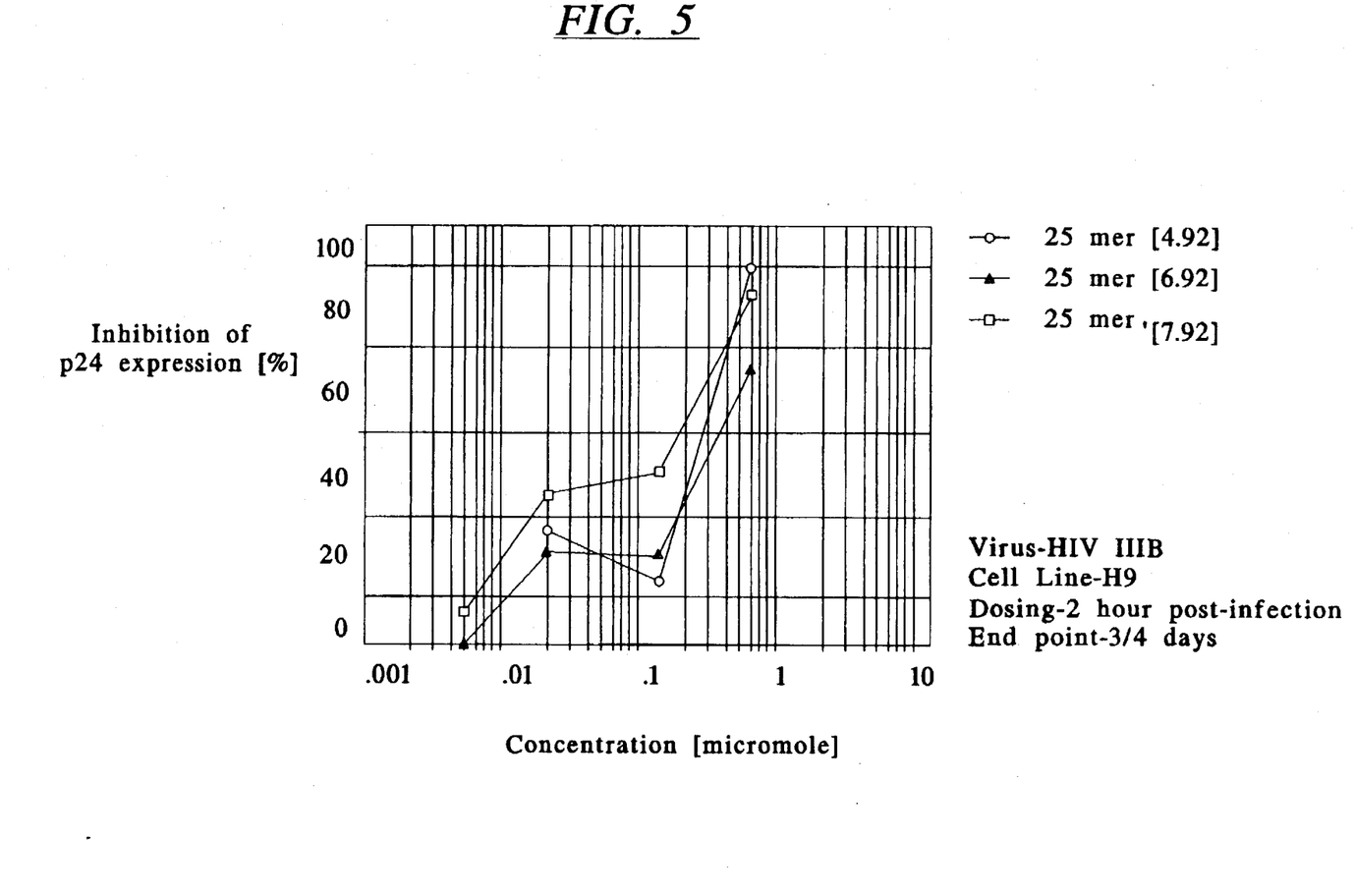
FIG. 5. is a graphic representation of the HIV-1 activity described in the Tables as % inhibition of p24 expression.
Figure 6:
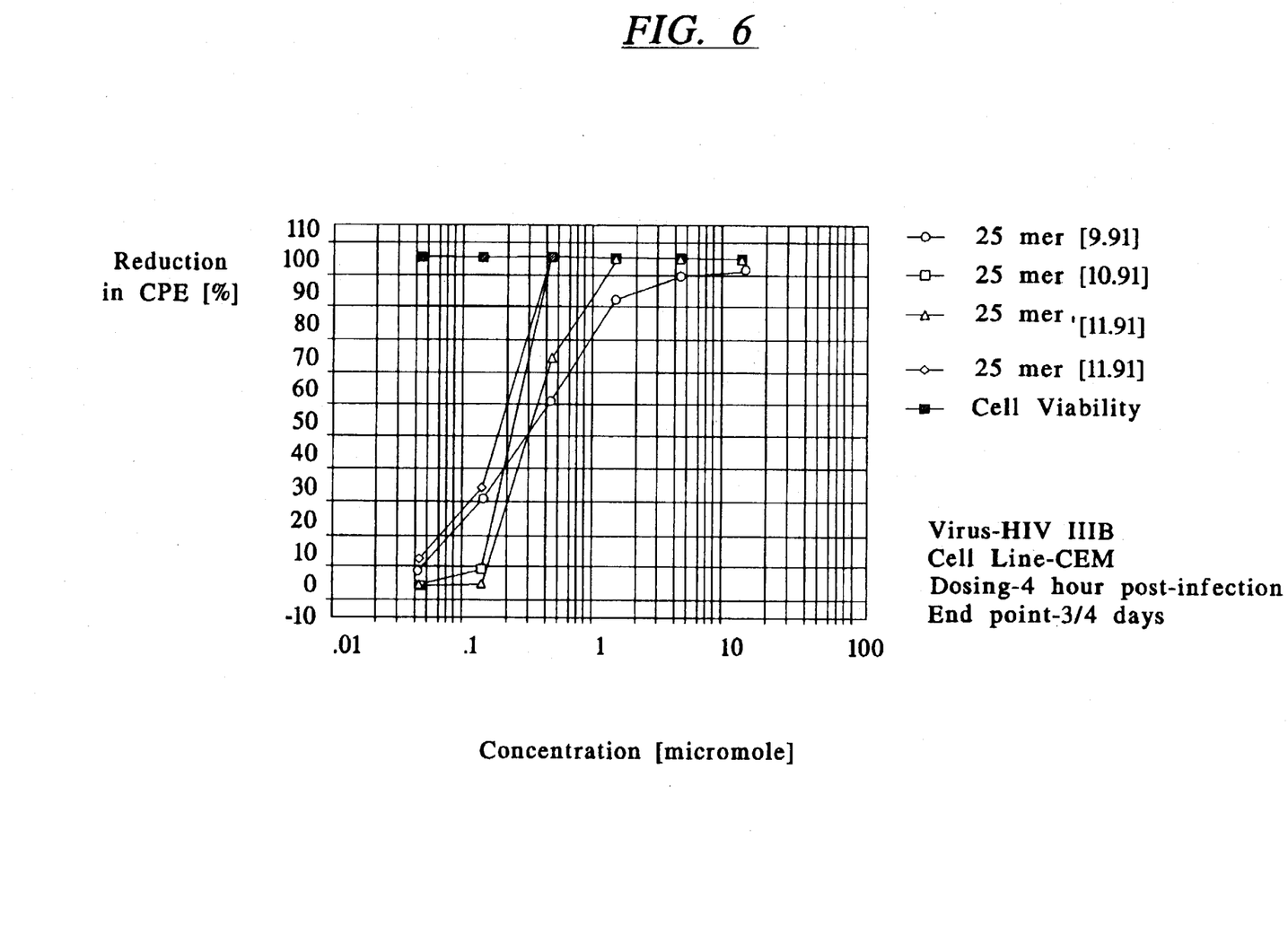
FIG. 6. is a graphic representation of HIV-1 activity described in the Tables as % reduction of CPE.

H9 cells are infected with HIV-1 (HTLVIII$_B$ or HTLVII-I$_{MN}$ strains) with 0.01–0.1TCID$_{50}$/cell for 1 hour at 37° C. TCID$_{50}$ is determined by infection of H9 cells with limiting dilutions of virus and subsequent cultures for two weeks. The cultures are prepared in quadruplicate at 10-fold dilution of HIV-1. After infection, unabsorbed virions are removed by washing. Infected cells are cultured in the presence of oligonucleotide concentrations (0.005, 0.02, 0.13, and 0.6 µM) for 3 to 4 days at 37° C. The level of HIV-1 expression is monitored by measuring p24 in supernatant with a monoclonal antibody-based p24 antigen capture test (DuPont). The results are summarized in TABLE 4. Cytotoxicity is determined by culturing uninfected cells with the 25 mer-for 3 to 4 days and counting the cells with a Coulter counter. The results are also shown in TABLE 4 and in FIG. 5.

TABLE 4

HIV p24 Antigen Assay

| Expt. # | Oligo. | Conc. µg/ml | Conc. µM | % Cell Survival | Inhibition of p24 (%) |
|---|---|---|---|---|---|
| 1 | 25mer | 25.0 | 2.9 | 0.93 | 90 |
| | | 5.0 | 0.5 | 1.03 | 89 |
| | | 1.0 | 0.1 | 0.94 | 15 |
| | | 0.2 | 0.02 | 0.97 | 26 |
| | AZT | 0.2 | 0.6 | 0.95 | 90 |
| | | 0.04 | 0.1 | 0.98 | 73 |
| | | 0.008 | 0.02 | 1.04 | 44 |
| | | 0.0016 | 0.005 | 1.08 | 6 |
| 2 | 25mer | 5.0 | | 0.93 | 66 |
| | | 11.0 | | 1.01 | 20 |
| | | 0.2 | | 1.07 | 21 |
| | | 0.04 | | 1.02 | — |
| 3 | 25mer | 10.0 | | 1.0 | 88 |
| | | 1.0 | | 1.0 | 12 |
| | | 0.1 | | 1.0 | — |
| | | 0.01 | | 1.0 | — |

These results show that the 25 mer is more effective at inhibiting p24 expression, and thus HIV-1 replication at lower concentrations than is AZT.

3. In chronically infected CEM cells

Chronically infected CEM cells are cultured in the presence of the 25 mer at concentration of 200, 64 and 20 µg/ml. Cells are then cultured at 37° C. At 24 and 48 hours of treatment, supernatants from treated cells are removed and assayed for the level of reverse transcriptase (RT) activity as described by Sarin et al. (*J. Natl. Cancer Inst.* (1987) 78:663–666). The level is compared to the level of RT in control untreated infected cells. The results are summarized in TABLE 5.

TABLE 5

Anti-HIV Activity of the 25mer In Chronically Infected Cells

| Oligo. | Conc. µg/ml | Time (hour) | % Inhibition of of RT |
|---|---|---|---|
| 25mer | 200 | 24 | 92 |
| | 64 | | 49 |
| | 20 | | — |
| | 200 | 48 | 87 |
| | 64 | | 53 |
| | 20 | | — |

The 25 mer was able to inhibit RT activity in this in vivo system, even after 2 days, unlike nucleotide analogs which appear to have no affect chronically infected cells.

B. Long term Infection Assays

Figure 7:
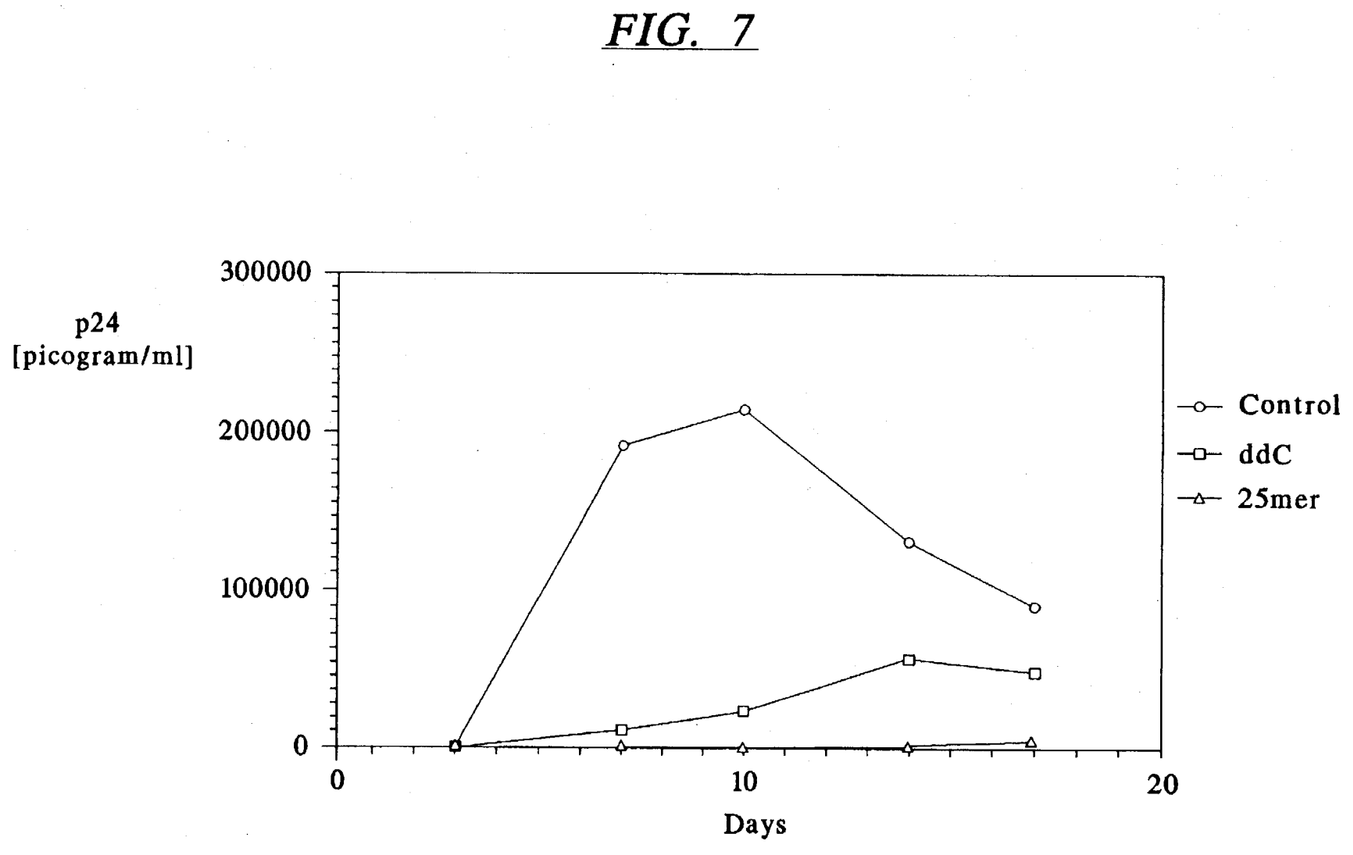
FIG. 7. is a graphic representation of a long term protection experiment, demonstrating the effectiveness of the 25 mer in inhibiting p24 expression until day 17 and the ineffectiveness of ddC.

H9 cells are infected with HIV-1 (HTLVIII$_B$) at 0.01–0.1 TCID$_{50}$/cell for 2 hours, washed to removed unabsorbed virions, diluted to $2 \times 10^5$ cells/ml and cultured at 37° C. Every 3 to 4 days cells are diluted to $2 \times 10^5$/ml then cultured in fresh medium containing 5 μg/ml (0.7 μM) of the 25 mer or ddC. At the time of splitting of cells, supernatant is removed and the level of p24 expression is measured by the antigen capture assay (Dupont). Results are shown in FIG. 7 and are summarized in TABLE 6.

TABLE 6

Inhibition of HIV-1 Replication by 25mer In Long Term Culture

|  | Control | 25mer | ddC |
|---|---|---|---|
| concentration (μM)→ | — | 0.60 | 0.05 |
| p24 expression (pg/ml) |  |  |  |
| day 3 | 489 | 21 (95*) | 124 (75*) |
| day 7 | 188,800 | 790 (99*) | 10,800 (94*) |
| day 10 | 210,400 | 380 (99*) | 17,300 (91*) |
| day 14 | 130,400 | 870 (95*) | 60,000 (56*) |
| day 17 | 95,600 | 5,800 (94*) | 54,000 (44*) |

*% inhibition of p24 compound compare with control

These results indicate that the 25 mer can inhibit p24 expression, and hence HIV-1 replication, with more efficiency than can ddC, and is much more active than ddC in the long term (>ten days). This may be because nucleotide analogs are more susceptible to nuclease digestion than are oligonucleotides with phosphorothioate linkages.

Figure 3:
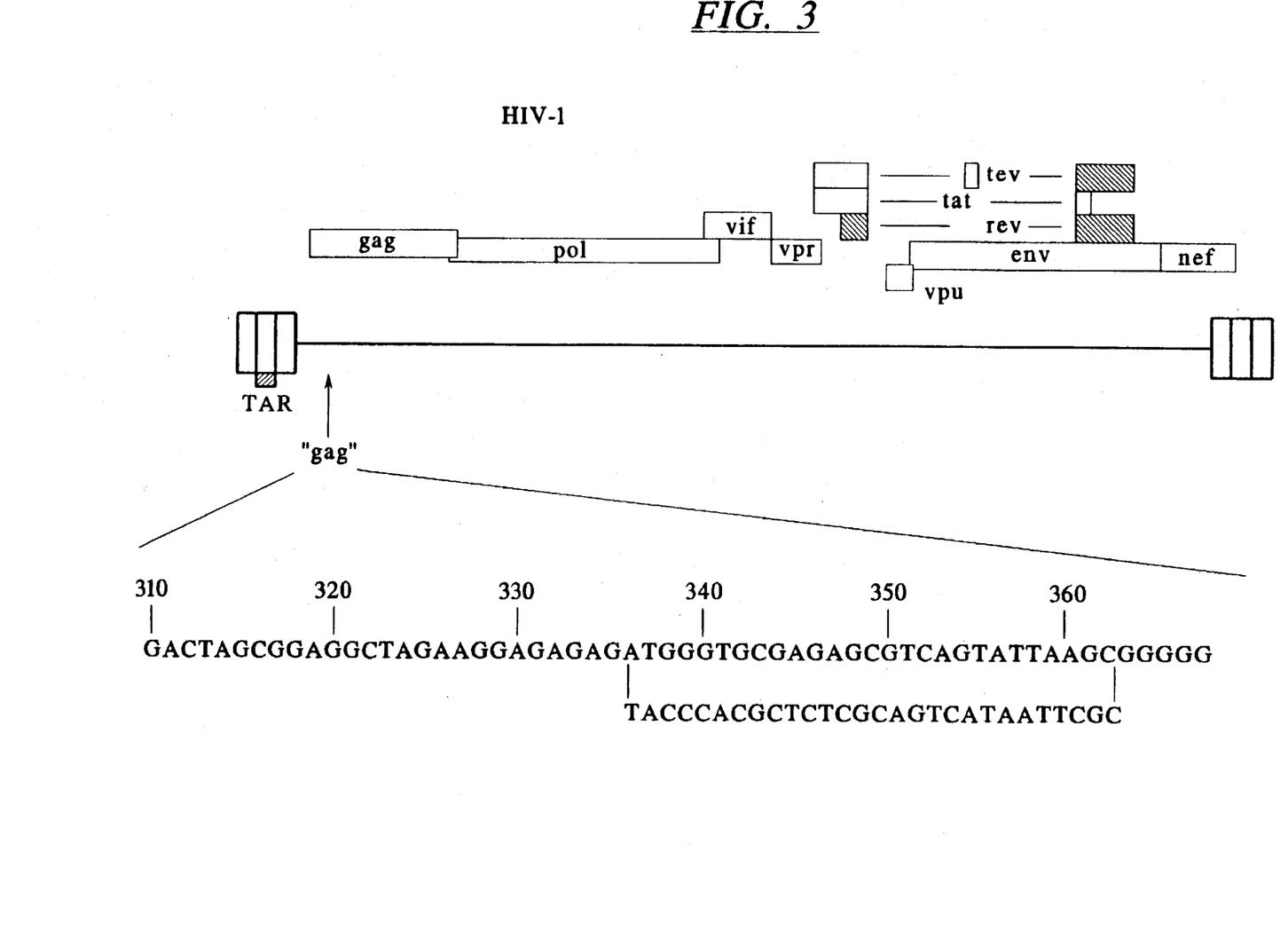
FIG. 3. is a schematic representation of the targeted gag initiation region (SEQ ID NO:14) and the 28 mer of Matsukura et al. (SEQ ID NO:15)
Figure 4:
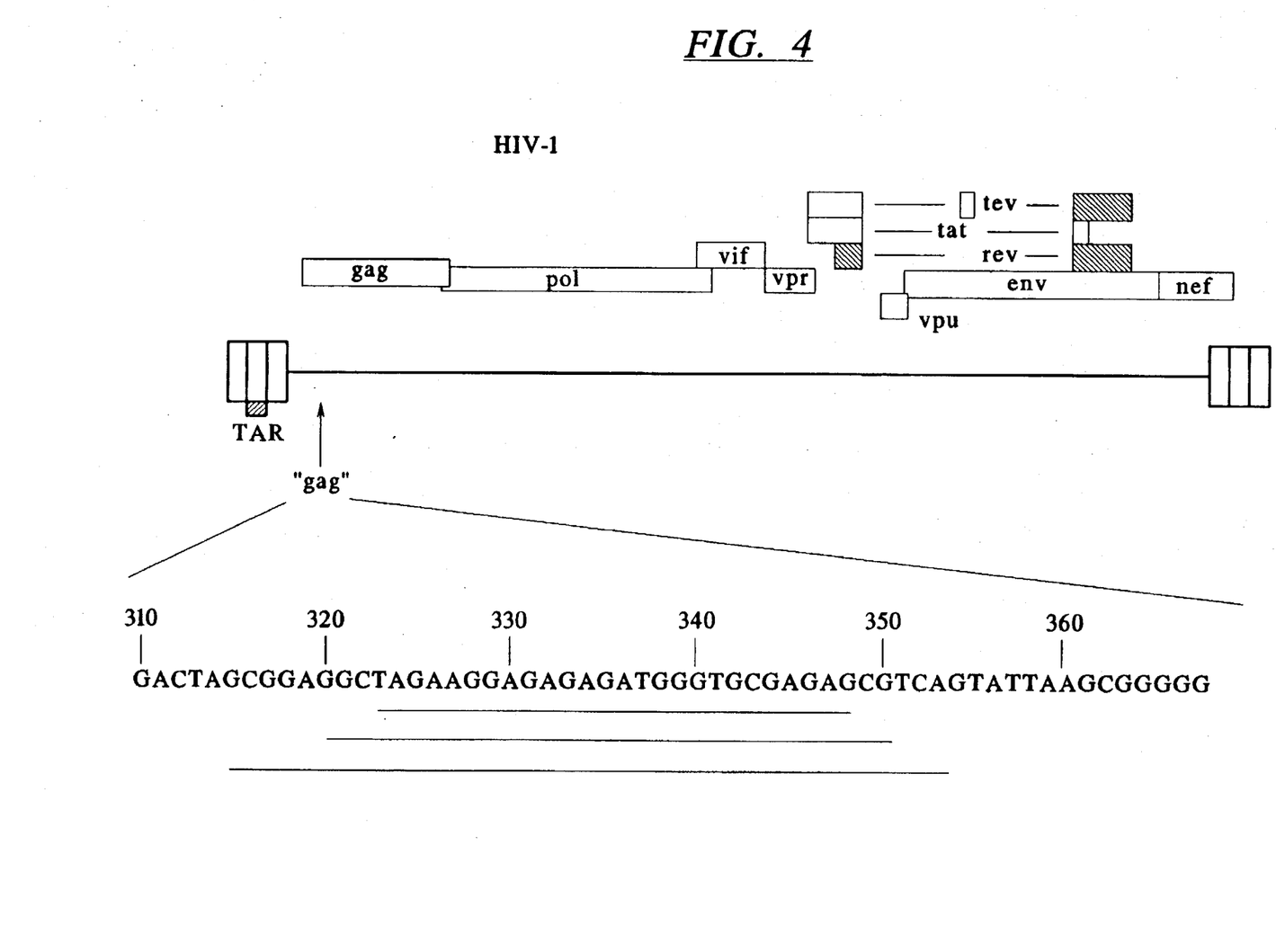
FIG. 4. is a schematic representation of the targeted gag initiation region (SEQ ID NO:14) and the sites to be covered by antisense oligonucleotides of the invention.

Thus, oligonucleotides of the invention are more specific, less toxic, and have greater nuclease resistance than many other chemotherapeutic agents designed to inhibit HIV-1 replication. In addition, they are more active in inhibiting viral replication than other known antisense oligonucleotides containing less than the 324 to 348 HIV-1 gag sequence. For example, the 20 mer set forth in the Sequence Listing as SEQ ID NO:10 is less active than the 25met of the invention. Additionally, a 28 mer described by Maktsukura et al. (in *Prospects for Antisense Nucleic Acid Therapy of Cancer and AIDS* Wiley-Liss, Inc., (1991) pp.159–178) (FIG. 3) which is complementary to a portion of the gag region overlapping region 324–348 is also much less active. This may be because the ribosome binding site (AUG) and regions flanking it are securely masked by the oligonucleotides of the invention that are at least 25 nucleotides in length. Also, when hybridized to this region, the oligonucleotides of the invention cannot be easily replaced by the ribosome, hence thwarting HIV infection. Furthermore, the conservation of this gag region results in the avoidance of escape mutants. This effect can be further increased by using oligonucleotides of the invention in conjunction with other anti-HIV oligonucleotides or anti-HIV drugs.

Those skilled in the art will recognize, or be able to ascertain, using no more than routine experimentation, numerous equivalents to the particular substances and procedures described herein. Such equivalents are considered to be within the scope and spirit of this invention, and are covered by the following claims.

What is claimed is:

1. The oligonucleotide having the nucleotide sequence set forth in the Sequence Listing as SEQ ID NO:1.

2. The oligonucleotide according to claim 1 in which at least one internucleotide linkage is a phosphorothioate linkage.

* * * * *